(12) United States Patent
Hamilton

(10) Patent No.: US 10,413,216 B2
(45) Date of Patent: Sep. 17, 2019

(54) BREATH TESTING APPARATUS

(71) Applicant: QuinTron Instrument Company, Inc., Milwaukee, WI (US)

(72) Inventor: Eric Lyle Hamilton, South Milwaukee, WI (US)

(73) Assignee: QUINTRON INSTRUMENT COMPANY, INC., Milwaukee, WI (US)

( * ) Notice: Subject to any disclaimer, the term of this patent is extended or adjusted under 35 U.S.C. 154(b) by 262 days.

(21) Appl. No.: 15/014,205

(22) Filed: Feb. 3, 2016

(65) Prior Publication Data

US 2017/0215764 A1    Aug. 3, 2017

(51) Int. Cl.
    *B65D 81/00*      (2006.01)
    *A61B 5/097*      (2006.01)

(52) U.S. Cl.
    CPC .................. *A61B 5/097* (2013.01)

(58) Field of Classification Search
    CPC ...................................................... A61B 5/097
    See application file for complete search history.

(56) References Cited

U.S. PATENT DOCUMENTS

| | | |
|---|---|---|
| 1,191,700 A | 7/1916 | Howes |
| 1,467,615 A | 9/1923 | Fairbanks |
| 2,795,223 A | 6/1957 | Stampe |
| 2,893,683 A | 7/1959 | Lane |
| 3,303,840 A | 2/1967 | Etzlinger |
| 3,388,705 A | 6/1968 | Grosshandler |
| 3,410,300 A | 11/1968 | Mondano |
| 3,426,745 A | 2/1969 | Farr |
| 3,437,449 A | 4/1969 | Luckey |
| 3,544,273 A | 12/1970 | McConnaughey |
| 3,602,531 A | 8/1971 | Patry |
| 3,734,692 A | 5/1973 | Lucker et al. |
| 3,777,571 A | 12/1973 | Jaeger |
| 3,817,108 A | 6/1974 | Principe et al. |
| 3,858,573 A * | 1/1975 | Ryan ..................... A61B 5/097 128/205.12 |
| 3,923,043 A | 12/1975 | Yanda |
| 3,924,832 A | 12/1975 | Babcock |
| 4,076,044 A | 2/1978 | Schindling |
| 4,161,307 A | 7/1979 | Clinch et al. |

(Continued)

FOREIGN PATENT DOCUMENTS

| | | |
|---|---|---|
| DE | 4028387 | 3/1992 |
| FR | 1294835 | 4/1962 |

(Continued)

OTHER PUBLICATIONS

European Search Report pertaining to EP17154042.0, dated Jun. 28, 2017, 6 pages.

(Continued)

*Primary Examiner* — Navin Natnithithadha
*Assistant Examiner* — Andrey Shostak
(74) *Attorney, Agent, or Firm* — Ryan Kromholz & Manion, S.C.

(57) ABSTRACT

A breath testing apparatus is provided with a mouthpiece, a collection chamber, and a discharge chute. A breath sample is captured within the collection chamber and transferred to an evacuated container through the discharge chute by a sample transfer assembly.

3 Claims, 2 Drawing Sheets

(56) References Cited

U.S. PATENT DOCUMENTS

| | | | |
|---|---|---|---|
| 4,327,741 A | 5/1982 | Watson et al. | |
| D266,695 S | 10/1982 | Trammil et al. | |
| 4,470,412 A | 9/1984 | Nowacki et al. | |
| 4,506,665 A | 3/1985 | Andrews et al. | |
| D280,765 S | 9/1985 | Alvino | |
| 4,544,273 A | 10/1985 | Berndt | |
| 4,579,826 A | 4/1986 | Bolton et al. | |
| 4,580,556 A | 4/1986 | Kondur | |
| 4,585,254 A | 4/1986 | Adams | |
| D283,914 S | 5/1986 | Garner | |
| 4,587,989 A | 5/1986 | Mayhew, Jr. | |
| 4,646,786 A | 3/1987 | Herder et al. | |
| 4,671,298 A | 6/1987 | Babb et al. | |
| D294,298 S | 2/1988 | Bush | |
| 4,809,692 A | 3/1989 | Nowacki et al. | |
| 4,821,737 A | 4/1989 | Nelson | |
| 4,827,921 A | 5/1989 | Rugheimer | |
| 4,832,015 A | 5/1989 | Nowacki et al. | |
| 4,850,953 A * | 7/1989 | Haber | A61F 2/0013 600/32 |
| 4,852,563 A | 8/1989 | Gross | |
| 4,852,583 A | 8/1989 | Walker | |
| D307,183 S | 4/1990 | Kalayjian | |
| 4,919,127 A | 4/1990 | Pell | |
| 4,938,210 A | 7/1990 | Shene | |
| 4,947,861 A | 8/1990 | Hamilton | |
| 4,953,547 A | 9/1990 | Poole, Jr. | |
| 5,012,803 A | 5/1991 | Foley et al. | |
| 5,012,804 A | 5/1991 | Foley et al. | |
| 5,042,500 A | 8/1991 | Norlien et al. | |
| 5,042,501 A | 8/1991 | Kenny et al. | |
| 5,062,423 A | 11/1991 | Matson et al. | |
| 5,066,597 A | 11/1991 | Stinson et al. | |
| 5,100,005 A | 3/1992 | Noble et al. | |
| D327,338 S | 6/1992 | Wallace | |
| 5,137,520 A | 8/1992 | Maxson et al. | |
| 5,140,993 A | 8/1992 | Opekun, Jr. et al. | |
| 5,165,393 A | 11/1992 | Kawaguchi | |
| 5,327,901 A | 7/1994 | Delente | |
| 5,346,089 A | 9/1994 | Brown et al. | |
| 5,432,094 A | 7/1995 | Delente | |
| 5,465,728 A | 11/1995 | Phillips | |
| 5,467,776 A | 11/1995 | Hamilton | |
| 5,711,306 A | 1/1998 | Guilluy | |
| 6,019,122 A | 2/2000 | Chen | |
| 6,368,558 B1 | 4/2002 | Suslick et al. | |
| 6,468,477 B1 | 10/2002 | Hamilton et al. | |
| 6,495,102 B1 | 12/2002 | Suslick et al. | |
| D691,717 S | 10/2013 | McClean et al. | |
| D714,435 S | 9/2014 | Maguire | |
| D722,688 S | 2/2015 | Hamilton | |
| 2004/0157281 A1 | 8/2004 | Hulkower | |
| 2012/0226183 A1* | 9/2012 | Christman | A61B 5/097 600/543 |
| 2014/0057141 A1* | 2/2014 | Mosso | H01M 8/20 429/51 |
| 2014/0127326 A1* | 5/2014 | Sood | A61B 5/082 424/649 |

FOREIGN PATENT DOCUMENTS

| | | |
|---|---|---|
| FR | 2497686 | 7/1982 |
| GB | 2064324 A | 6/1981 |
| GB | 2230456 | 10/1990 |
| WO | WO 9311817 | 6/1993 |

OTHER PUBLICATIONS

Rakow, N. A.; Suslick, K. S. "A Colorimetric Sensor Array for Odour Visualization" Nature, vol. 406, Aug. 17, 2000, 4 pages.

Webpage: www.chemsensing.com/hepatotoxicity.html—ChemSensing, Hepatotoxicity, Dec. 29, 2004, 2 pages.

Webpage: www.chemsensing.com/elisa.html—ChemSensing, ELISA, Dec. 29, 2004, 1 page.

\* cited by examiner

BREATH TESTING APPARATUS

BACKGROUND OF THE INVENTION

This invention relates to the field of sampling air from the lungs and specifically to the field of obtaining a sample of a person's air, including alveolar air from the alveoli of the lungs of a person.

Air from the lungs of a person can be used for many different types of testing that would otherwise require the person to undergo an invasive procedure. For example, alveolar air can be analyzed for, but not limited to, the noninvasive diagnosis of a wide variety of conditions including the noninvasive diagnosis of stomach infections related to a high incidence of ulcers, enzymatic deficiencies, and metabolic conditions and/or abnormalities. Crucial to any such testing is the ability to get an accurate sample containing a sufficient volume of air representative of true alveolar air, necessary for specific testing.

Hydrogen and methane are produced in the digestive system primarily only by the bacterial fermentation of carbohydrates (sugars, starches or vegetable fibers), so either of these gases appear in the expired air, it is usually a signal that carbohydrates or carbohydrate fragments have been exposed to bacteria, permitting such fermentation to take place. Levitt, M. D. Production and excretion of hydrogen gas in man. New Engl. J. Med 1968; 281:122 (incorporated herein by reference). The generation of H2 and/or CH4 will result in the reabsorption of some of these gases into the blood stream from the site of their digestion, and they will appear in the expired air.

Bacteria are ordinarily not present in significant numbers in the small intestine, where digestion and absorption of sugars take place. Therefore, when a challenge dose (eg. lactose) is ingested, the level of hydrogen in alveolar air will rise significantly within one to two hours (depending on the intestinal transit time) only if the sugar is not digested and, therefore reaches the colon.

The breath-H2 test is a simple non-invasive procedure which is readily accepted by patients and staff (Metz, G.; Jenkins, D. L.; Peters, T. J,; Newman, A.; Blendis, L. M. Breath hydrogen as a diagnostic method for hypolactasia. Lancet. 1975; 1 (7917):1155-7, incorporated herein by reference), and which has greater reliability and acceptability than the blood test, according to most reports in the literature (DiPalma, J. A.; Narvaez, R. M. Prediction of lactose malabsorption in referral patients. Dig Dis Sci. 1988; 33:303, incorporated herein by reference, and Davidson, G. P.; Robb, T. A. Value of breath hydrogen analysis in management of diarrheal illness in childhood: Comparison with duodenal biopsy. J Ped Gastroenterol Nutr. 1985; 4:381-7; Fernandes, J.; Vos, C. E.; Douwes, A, C,; Slotema, E.; Degenhart, H. J. Respiratory hydrogen excretion as a parameter for lactose malabsorption in children. Amer J Clin Nutr. 1978; 31:597-602; Newcomer, A. D.; McGill, D. B.; Thomas, R. J.; Hofmann, A. F. Prospective comparison of indirect methods for detecting lactase deficiency. New Engl J Med. 1975; 293:1232-6; Douwes, A. C.; Fernandes, J.; Degenhart H. J. Improved accuracy of lactose tolerance test in children, using expired H2 measurement. Arch Dis Child. 1978; 53:939-42; Solomons, N. W.; Garcia-Ibanez, R.; Viteri, F. E. Hydrogen breath test of lactose absorption in adults: The application of physiological doses and whole cow's milk sources. Amer J Clin Nutr. 1980; 33:545-54; each incorporated by reference).

The lower dose of lactose usually does not cause the discomfort and explosive diarrhea frequently seen by malabsorbers who are given the large dose required for the blood test.

A study with over 300 patients showed that G-I symptoms after a lactose challenge are strongly associated with the amount of H2 excreted, and the relationship between blood glucose change and symptom-severity was less evident. Jones, D. V.; Latham, M. C.; Kosikowski, F. V.; Woodward, G. Symptom response to lactosereduced milk in lactose-intolerant adults. Amer J Clin Nutr. 1976; 29(6):633-8, incorporated by reference.

False-positive breath-tests are rare, and when they occur they are usually caused by improperly doing the test—allowing the subject to smoke, to sleep or to eat shortly before or during the test. Bacterial overgrowth (from the colon, retrograde into the small intestine) can also produce a false-positive breath-test, but it is usually preceded by an elevated fasting breath-H2 level and the response is seen soon after the sugar is ingested (within 20-30 minutes).

The incidence of false-negative results with the breath-test is well below that seen with the blood test. False-negative results are reported to be from 5-15% of all lactose malabsorbers. Filali, A.; Ben Hassine, L.; Dhouib, H.; Matri, S.; Ben Ammar, A.; Garoui, H. Study of malabsorption of lactose by the hydrogen breath test in a population of 70 Tunisian adults. Gastroenterol Clin Biol. 1987; 11:554-7; Douwes, A. C.; Schaap, C.; van der Kleivan Moorsel, J. M. Hydrogen breath test in school children. Arch Dis Child. 1985; 60:333-7; Rogerro, P.; Offredi, M. L.; Mosca, F.; Perazzani, M.; Mangiaterra, V.; Ghislanzoni, P.; Marenghi, L.; Careddu, P. Lactose absorption and malabsorption in healthy Italian children: Do the quantity of malabsorbed sugar and the small bowel transit time play roles in symptom production? J Pediatr Gastroenterol Nutr. 1985 (February); 4(1):82-614; each incorporated by reference. This is due to a variety of causes. Many of the false-negative reports can be avoided by measuring methane in addition to hydrogen because some methanogenic flora convert colonic H2 to CH4. Cloarac, D.; Bornet, F.; Gouilloud, S.; Barry, J. Ll.; Salim, B.; Galmiche, J. P. Breath hydrogen response to lactulose in healthy subjects: relationship to methane producing status. Gut. 1990 (March); 31:300-4; incorporated by reference.

SUMMARY OF THE INVENTION

In accordance with the present invention, a testing apparatus is provided. A breath collection apparatus comprising a breath entryway or mouthpiece is coupled to a first one-way coupling, which is preferably, but not necessarily, a flutter valve. Breath is expelled into the mouthpiece and through the one-way coupling. A collection chamber is coupled to said breath entryway by said first one-way coupling, and a second one-way coupling, also which is preferably, but not necessarily, a flutter valve coupled to said collection chamber to allow a first waste portion of exhaled breath to escape the collection chamber. When the breath is completed, both one-way couplings will close, trapping an end-expiration breath sample within the collection chamber. A sample transfer assembly coupled to said collection chamber allows for an evacuated air chamber to be selectively coupled to said sample transfer assembly, and the evacuated air chamber recovers a portion of the end-expiration breath sample within the collection chamber. In a preferred embodiment, a discharge chute is coupled to said collection chamber about said sample transfer assembly, said discharge chute comprising a proximal end for coupling to said collection chamber, and a distal end for receiving said evacuated air chamber.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention.

Figure 1:
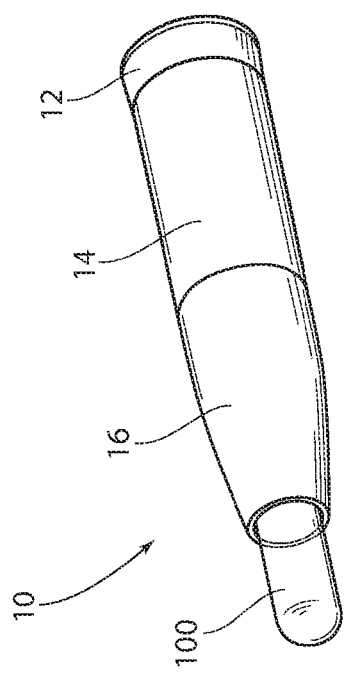
FIG. 1 is a perspective view of a sample collection apparatus of the present invention, with an evacuated air chamber inserted into a distal end of a discharge chute.

Referring now to FIG. 1 a perspective view of a sample collection apparatus 10 of the present invention is shown. A mouthpiece 12 comprising a breath entryway is shown, to allow breath to pass to collection chamber 14. A breath discharge chute 16 receives an evacuated air chamber 100 that receives an end-expiration breath sample (described later) from within the collection chamber 14.

Figure 2:
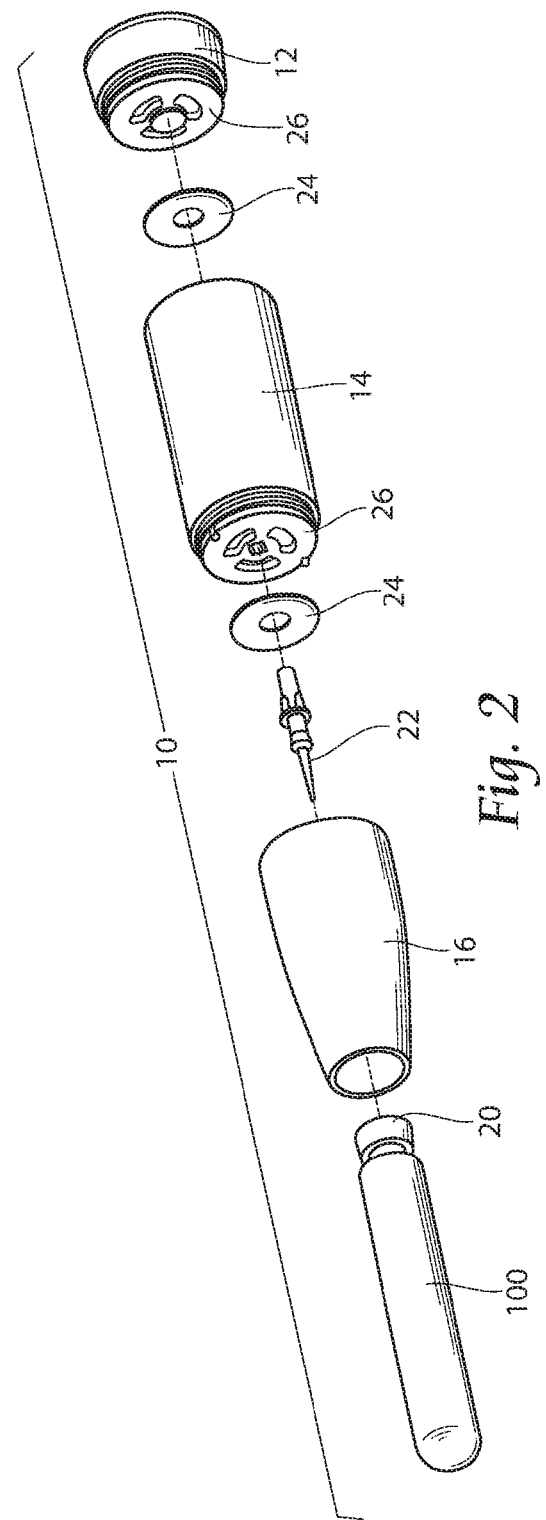
FIG. 2 is an exploded perspective view of a sample collection apparatus of the present invention.

Referring now to FIG. 2, an exploded perspective view of a sample collection apparatus 10 of the present invention is shown. Mouthpiece 12 is either integrally formed or coupled with a one-way discharge assembly 26. Positive pressure from a breath, through the mouthpiece 12, causes flexible ring 24 to flex, and allow air to pass into collection chamber 14 at an upstream end of collection chamber 14. Flexible ring 24, is preferably, but not necessarily, a flutter valve. Another one-way discharge structure 24, again coupled to a flexible ring 24 (and again preferably, but not necessarily, a flutter valve), is coupled to a downstream end of collection chamber 14. Coupled to the interior of collection chamber 14 is discharge needle 22, which provides a selective passageway from breath between collection chamber 14 and ultimately evacuated air chamber 100, which is coupled to discharge needle 22 through discharge chute 16.

Figure 3:
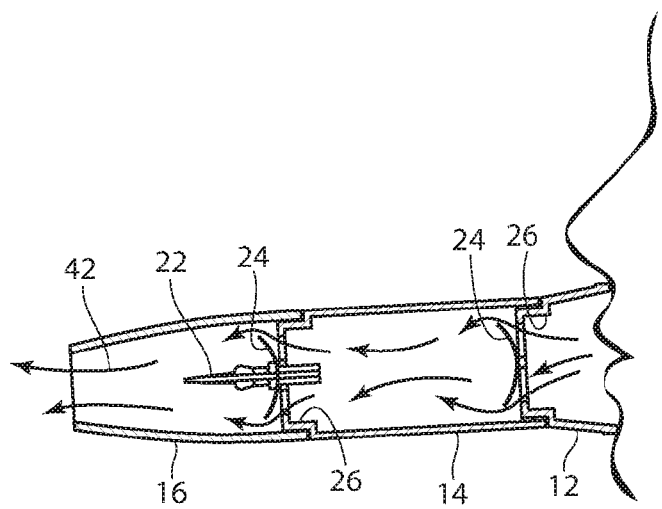
FIG. 3 is an in-use side cross-sectional view of a sample collection apparatus, shown collecting a breath sample.

Referring now to FIG. 3, an in-use side cross-sectional view of sample collection apparatus 10 is shown. A patient has pressed a mouth to mouthpiece 12 and began exhalation. The first volume of breath 42 evacuates background air from within collection chamber 14, and first volume of breath 42, being not the most desirable for alveolar air sampling, is expelled through discharge chute 16 without capture. Positive pressure from the breath sample flexes flexible rings 24, allowing air to continue to flow through collection chamber 14, into discharge chute 16.

As the breath stops, the positive pressure from the breathing stops as well, allowing flexible rings 24 to return to their static position, flush against one-way discharge structures 26 at the upstream and downstream ends of collection chamber 14. As the flexible rings 24 seal the collection chamber 14, end-expiration breath sample 40 is captured in collection chamber 14. To retrieve the end-expiration breath sample 40 for convenient sampling by gas chromatography equipment, it is desirable to collect end-expiration breath sample 40 in an evacuated air chamber 100 (a test tube). Evacuated air chamber 100 is of a volume V1, which is preferably a smaller volume than volume V2 of the collection chamber 14, so that evacuated air chamber 100 collects only end-expiration breath sample 40 from the collection chamber 14, and not outside air drawn through collection chamber 14.

Figure 4:
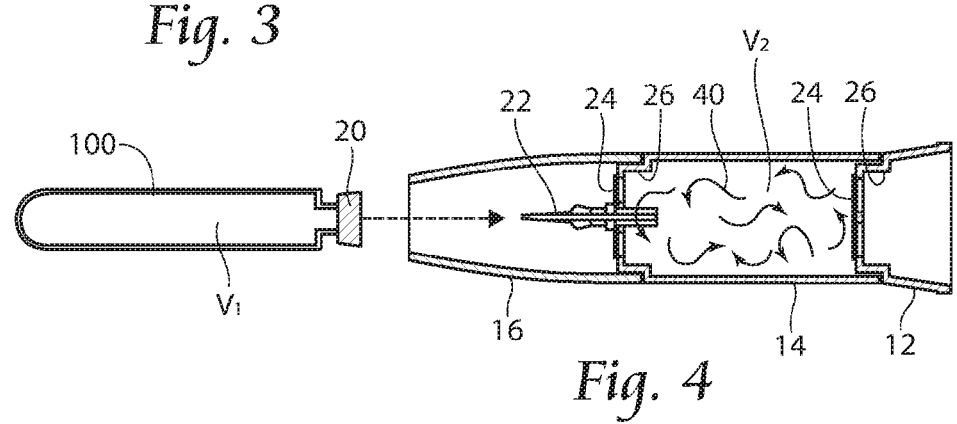
FIG. 4 is a side cross-sectional view of a sample collection apparatus, with an evacuated air chamber being inserted into a distal end of the discharge chute.
Figure 5:
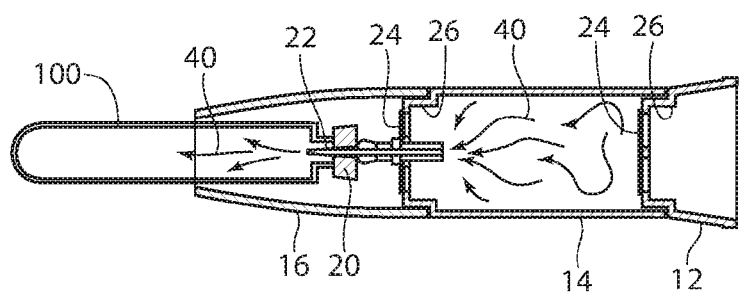
FIG. 5 is a side cross-sectional view of a sample collection apparatus, with an evacuated air chamber being inserted onto a discharge needle within the discharge chute.
Figure 6:
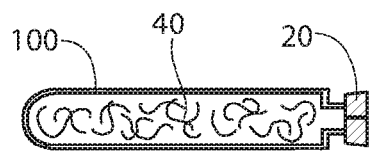
FIG. 6 shows a collected end-expiration breath sample.

Evacuated air chamber 100 is inserted into a distal end of the discharge chute 16 as shown in FIG. 4, and as shown in FIG. 5, evacuated air chamber 100 is inserted onto discharge needle 22, piercing a septum 20 (preferably self-sealing) of air chamber 100. The evacuated air chamber 100 then retrieves end-expiration breath sample 40 from collection chamber 14. After air chamber 100 has retrieved end-expiration breath sample 40 from collection chamber 14, the air chamber 100 can be withdrawn from the discharge needle 22 within discharge chute 16. The air chamber 100 containing end-expiration breath sample 40 can then be processed in a laboratory for target analytes as desired.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention.

I claim:

1. A breath collection apparatus comprising:
    a breath entryway;
    a first one-way coupling;
    a collection chamber having proximal and distal ends and coupled at its proximal end to said breath entryway by said first one-way coupling;
    a second one-way coupling coupled to the distal end of said collection chamber;
    a sample transfer assembly coupled to the distal end through said second one-way coupling of said collection chamber, said sample transfer assembly configured to be selectively coupled to an evacuated air chamber to collect a portion of an end-expiration breath sample contained within the collection chamber, said sample transfer assembly comprising a needle for penetrating a septum sealing the evacuated air chamber; and
    a discharge chute coupled to the distal end of said collection chamber about said sample transfer assembly, said discharge chute comprising a proximal end for coupling to said collection chamber, and a distal end for receiving said evacuated air chamber, said second one-way coupling arranged, in operation, within said discharge chute,
    wherein the breath entryway, the first one-way coupling, the collection chamber, the second one-way coupling, the sample transfer assembly and the discharge chute are axially aligned with one another.

2. The breath collection apparatus according to claim 1, the apparatus further comprising said evacuated air chamber selectively coupled to said sample transfer assembly.

3. The breath collection apparatus according to claim 1, wherein at least one of said one-way couplings comprises a flutter valve.

* * * * *